United States Patent [19]
Wright et al.

[11] Patent Number: 5,674,279
[45] Date of Patent: Oct. 7, 1997

[54] ANNULOPLASTY AND SUTURE RINGS

[75] Inventors: John T. M. Wright, Conifer; Donald P. Elliott, Denver, both of Colo.

[73] Assignee: Medtronic, Inc., Minneapolis, Minn.

[21] Appl. No.: 437,448

[22] Filed: Jun. 29, 1995

Related U.S. Application Data

[62] Division of Ser. No. 188,624, Jan. 28, 1994, abandoned, which is a division of Ser. No. 933,339, Aug. 21, 1992, Pat. No. 5,306,296, which is a continuation of Ser. No. 826,405, Jan. 27, 1992, Pat. No. 5,201,880.

[51] Int. Cl.$^6$ ........................................ A61F 2/24
[52] U.S. Cl. ........................................... 623/2
[58] Field of Search ........................... 623/2, 900

[56] References Cited

U.S. PATENT DOCUMENTS

| | | |
|---|---|---|
| 3,365,728 | 1/1968 | Edwards . |
| 3,466,671 | 9/1969 | Siposs . |
| 3,491,376 | 1/1970 | Shiley . |
| 3,524,202 | 8/1970 | Cromie . |
| 3,534,411 | 10/1970 | Shiley . |
| 3,656,185 | 4/1972 | Carpenter . |
| 3,691,567 | 9/1972 | Cromie . |
| 4,042,979 | 8/1977 | Angell . |
| 4,055,861 | 11/1977 | Carpentier . |
| 4,164,046 | 8/1979 | Cooley . |
| 4,182,339 | 1/1980 | Hardy . |
| 4,217,665 | 8/1980 | Bex . |
| 4,259,753 | 4/1981 | Liotta . |
| 4,263,680 | 4/1981 | Reul . |
| 4,290,151 | 9/1981 | Massana . |
| 4,339,831 | 7/1982 | Johnson . |
| 4,451,936 | 6/1984 | Carpentier . |
| 4,477,930 | 10/1984 | Totten . |
| 4,602,911 | 7/1986 | Ahmadi . |
| 4,680,031 | 7/1987 | Alonso . |
| 4,702,250 | 10/1987 | Ovil . |
| 4,728,328 | 3/1988 | Hughes . |
| 4,834,755 | 5/1989 | Silvestrini . |
| 4,863,460 | 9/1989 | Magladry . |
| 4,865,600 | 9/1989 | Carpentier . |
| 4,888,009 | 12/1989 | Lederman . |
| 4,917,698 | 4/1990 | Carpentier . |
| 5,061,277 | 10/1991 | Carpentier . |
| 5,064,431 | 11/1991 | Gilbertson . |
| 5,104,406 | 4/1992 | Curcio . |
| 5,206,880 | 4/1993 | Wright . |
| 5,306,296 | 4/1994 | Wright . |

OTHER PUBLICATIONS

"Clinical & Hemodynamic Performance of a Totally Flexible Prosthetic Ring For Atrioventricular Valve Reconstruction" by Duren et al., in The Annuals of Thoracic Surgery, vol. 22, No. 5, Nov. 1976.

"Tricuspid Valve Repair Using a Flexible Linear Reduer" by Bex et al., in Journal of Cardiac Surgery, vol. 1, No., 1986.

"The Relationship of Mitral Annular Shape to the Diagnosis of Mitral Valve Prolapse", by Levine et al., in Circulation, vol. 75, No. 4, Apr., 1987.

"The Mitral Valve, A Pluridiscipliary Approach", by Tsakiris, Chapter 3 Publishing Sciences Groups, Inc., Acton, MA.

"Long–Term Follow–Up After Mitral Valve Reconstruction: Incidence of Postoperative Left Ventricular Outflow Obstruction", by Galler et al., in Circulation, vol. 74, (suppl 1) Sep. 1986.

"Surgical Management Of Acquired Tricuspid Valve Disease", Carpentier et al., in Journal of Thoracic & Cardiovascular Surgery, 67:53–65, Jan., 1974.

*Primary Examiner*—Michael J. Milano
*Attorney, Agent, or Firm*—Reed A. Duthler; Harold R. Patton

[57] ABSTRACT

Adjustable, flexible suture rings, tricuspid and tricuspid annuloplasty rings having internal drawstrings that emerge from the rings on the annular faces so that the drawstring knots are out of the bloodstream, the drawstrings being contained in clearly marked channels, the mitral ring having a curved semi-flexible stiffener member in the anterior segment to maintain intertrigonal distance during implantation are disclosed.

1 Claim, 10 Drawing Sheets

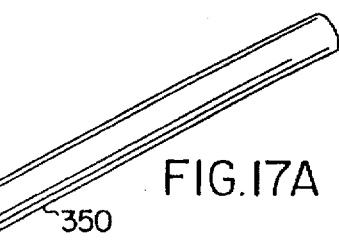
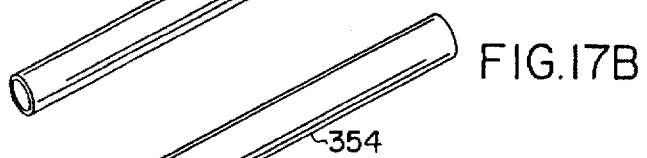
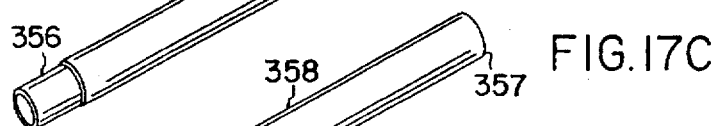
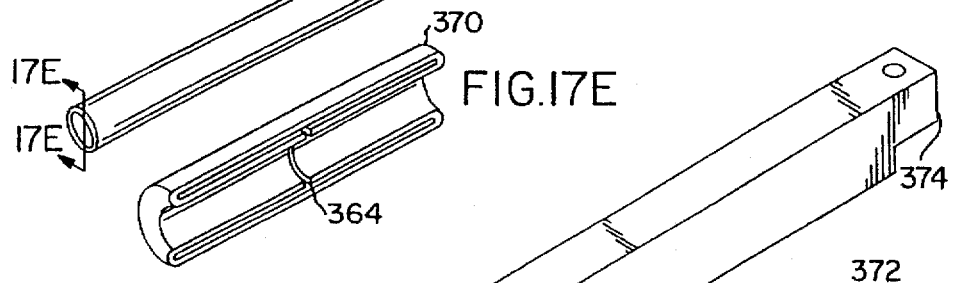
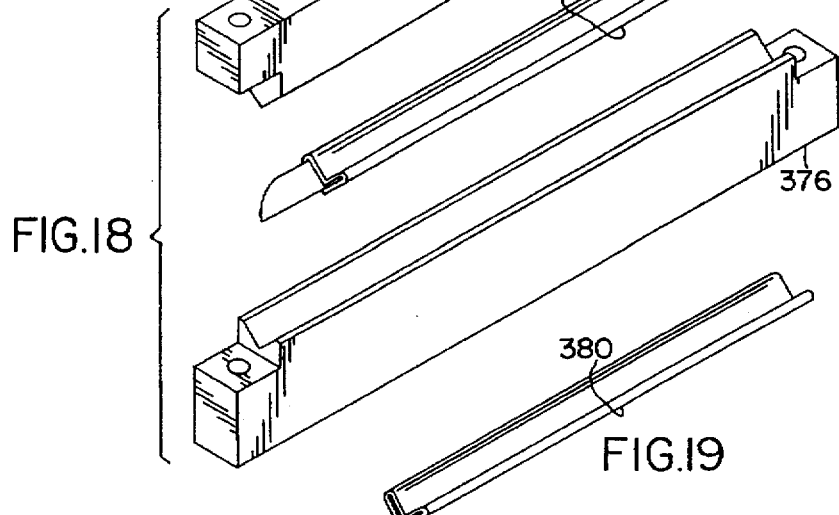
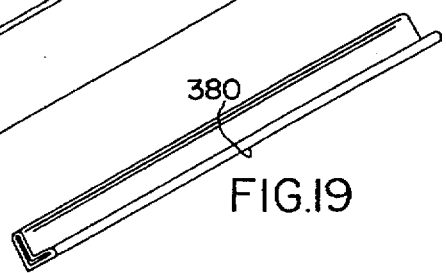

ANNULOPLASTY AND SUTURE RINGS

CROSS-REFERENCE TO RELATED APPLICATION

This is a divisional of application Ser. No. 08/188,624 filed on Jan. 28, 1994 now abandoned which is a divisional of Ser. No. 07/933,339 filed Aug. 21, 1992 now U.S. Pat. No. 5,306,296 which is a continuation of Ser. No. 826,405 filed on Jan. 27, 1992 now U.S. Pat No. 5,201,880.

BACKGROUND OF THE INVENTION

This invention relates to a prosthesis for use in the surgical correction of certain mitral or tricuspid valve disorders. There are two atrio-ventricular valves in the heart. That on the left side of the heart known as the mitral valve, and that on the right side known as the tricuspid valve. Both valves are subject to damage that requires that the valves be repaired or replaced. Clinical experience has shown that repair of the valve, where this is technically possible, produces better long term results than does valve replacement. The mitral and tricuspid valve differ significantly in anatomy. Whereas the annulus of mitral valve is somewhat "D" shaped, the annulus of the tricuspid valve is more nearly circular.

The effects of valvular dysfunction vary. Mitral regurgitation has more severe physiological consequences to the patient that does tricuspid valve regurgitation, a small amount of which is tolerated quite well. In patients with valvular insufficiency it is increasingly common surgical practice to retain the natural valves, and to attempt to correct the defects. Many of the defects are associated with dilation of the valve annulus. This dilatation not only prevents competence of the valve but also results in distortion of the normal shape of the valve orifice. Remodelling of the annulus is therefore central to most reconstructive procedures on the mitral valve.

Many procedures have been described to correct pathology of the valve leaflets and their associated chordal tendinae and papillary muscles. In mitral repairs it is essential to preserve the normal distance between the two fibrous trigones. The trigones almost straddle the anterior leaflet portion of the annulus. Between the left and right fibrous trigones the mitral annulus is absent (as described by Tsakiris A G. "The physiology of the mitral valve annulus" in The mitral valve—a pluridisciplinary approach. ed Kalmanson D. Publishing Sciences Group, Acton, Mass. 1976, pg 21–26). This portion of the mitral valve apparatus is formed by the change of the anterior of the base of the aorta into the (so called) sub-aortic curtain, and hence into the anterior leaflet of the mitral valve. A significant surgical diminution of the inter-trigonal distance could cause left ventricular outflow obstruction. Thus it is highly desirable to maintain the natural inter-trigonal distance during and following mitral valve repair surgery. Consequently, when a mitral valve is repaired (be it the posterior or anterior leaflet) the result is generally a reduction in the size of the posterior segment of the mitral valve annulus.

As a part of the mitral valve repair it is either necessary to diminish (i.e. constrict) the involved segment of the annulus so that the leaflets may coapt correctly on closing, or to stabilize the annulus to prevent post-operative dilatation from occurring. Either is frequently achieved by the implantation of a prosthetic ring in the supra annular position. The purpose of the ring is to restrict and/or support the annulus to correct and/or prevent valvular insufficiency. However, it is important not to over restrict the annulus or an unacceptable valvular stenosis would result. As described above, in mitral valve repair, constriction of the mitral annulus should take place only in the area of the posterior section of the valve annulus. Shortening of the posterior portion of the mitral valve annulus may be accomplished in several ways. Firstly, by implanting a substantially inexpansible ring (smaller in size than the annulus). With this type of device, the surgeon must accurately choose the size of ring that will just prevent insufficiency, yet will not cause significant valvular stenosis. Secondly, by a using a contractible ring that may be plicated during implantation. This type has the disadvantage that the surgeon must then accurately judge not only the ring size to use, but also how to space the implanting sutures in the ring and the annulus so that when implanted, insufficiency is minimized, yet there will be no significant valvular stenosis. Thirdly, and preferably, by a substantially inexpansible ring that may be contracted only in appropriate segments (and not in the anterior portion). The natural inter-trigonal distance should be maintained, and the anterior leaflet should not be diminished in circumference.

In tricuspid valve repair, constriction of the annulus usually takes place in the posterior leaflet segment and in a small portion of the adjacent anterior leaflet. The septal leaflet segment is not usually required to be shortened.

Various prostheses have been described for use in conjunction with mitral or tricuspid valve repair. Each has disadvantages. The ring developed by Dr. Alain Carpentier (U.S. Pat. No. 3,656,185) is rigid and flat. Although widely used, criticism of its inflexibility preventing the normal alteration in size and shape of the mitral annulus with the cardiac cycle has been widespread. The complication of left ventricular outflow tract obstruction has been described in association with this device. This complication can take the form of a decrease in the dimensions of the left ventricular outflow tract, or systolic anterior motion of the anterior leaflet of the valve. Both complications were reported by Geller M, Kronzon I, Slater J et al. "Long-term follow-up after mitral valve reconstruction: incidence of postoperative left ventricular outflow obstruction". Circulation 1986;74 (suppl I) I-99–103. They implanted Carpentier rings in sixty-five patients. All sixty surviving patients were restudied 1–55 months postoperatively. All showed a significant decrease in the dimensions of the left ventricular outflow tract, and 6 patients (10%) also had systolic anterior motion (SAM). Another complication of the Carpentier ring has been inflow obstruction. This complication associated with its use in tricuspid valves was reported by Carpentier et al. in nine of seventeen patients (Carpentier A, Deloche A, Hanania G, et al. "Surgical management of acquired tricuspid valve disease". J Thorac Cardiovasc Surg 1974;67:53–65). In addition, the Carpentier ring has the disadvantage of not being of adjustable size. Thus the surgeon has to accurately judge the correct size of ring needed to reduce the annulus size and produce a competent valve.

An open ring valve prosthesis was described in U.S. Pat. No. 4,164,046 comprising a uniquely shaped open ring valve prosthesis having a special velour exterior for effecting mitral and tricuspid annuloplasty. This ring was not adjustable in size during or following implantation. The fully flexible annuloplasty ring described by Carlos D. Duran and Jose Luis M. Ubago, "Clinical and Hemodynamic Performance of a Totally Flexible Prosthetic Ring for Atrioventricular Valve Reconstruction" Annals of Thoracic Surgery, (No.5), 458–463, (November 1976) could only be shortened in the posterior segment by the placement of plicating sutures. The judgement of the position, size and spacing of these sutures requires skill and experience. However, inappropriate suture placement in the anterior segment could cause undesirable intra-trigonal shortening. Adjustable annuloplasty rings were described by Dr. William Angell (U.S. Pat. No. 4,042,979) and Dr. Miguel Puig-Massana (U.S. Pat. No. 4,290,151). Both incorporate drawstrings capable of reducing the size of the posterior portion of the ring. The former contains a rigid or flexible member in the anterior leaflet portion of the ring. The latter ring is also adjustable but fully flexible. With this device the use of a continuous implantation suture was recommended rather than the more generally used interrupted sutures. With the Puig-Massana ring the use of interrupted sutures would be likely to interfere with the internal drawstrings. However, should a continuous suture be used for implantation, and the ring then contracted by the internal drawstrings, loosening of the continuous suture would be caused by the reduction in the circumference of the annulus. A further disadvantage of Puig-Massana's ring is that following the tightening of the drawstrings, a bulky knot is formed on the atrial surface of the ring. Hence, the knot lies in the direct blood flow path into the inflow of the valve. Should a thrombus form on the knot it could later embolize. In addition, should the surplus drawstrings be cut too close to the knot, there is the danger of the knot becoming undone. Conversely, should significant surplus drawstrings tails remain, abrasion of the valve leaflets could occur. The adjustable ring by Dr. Ali Ahmadi has the disadvantage of being circular, which is not an appropriate shape, particularly for the mitral annulus.

The rigid rings described above were probably conceived on the assumption that the mitral annulus is "D" shaped and lies in a single flat plane. That this was a misconception was shown by Levine, R. A., Triulzi, M. O., Harrigan P., and Weyman, A. E. "The relationship of mitral annular shape to the diagnosis of mitral valve prolapse", Circulation 75, No. 4, 756–767, 1987. This work shows that the mitral valve annulus is a complex and mobile structure and demonstrated that the mitral valve takes the form of a central, elliptical portion of a hyperbolic paraboloid or saddle shaped surface. It is clear that imposing a flat ring or even a segment of a flat ring would distort the annulus and could cause left ventricular outflow tract obstruction. The device which is the subject of this invention does not have these disadvantages.

U.S. Pat. No. 5,104,407, Lam et al, filed and issued subsequent to applicants' invention described herein describes an annuloplasty ring that has a rigid portion extending out of the plane of the ring joined with a flexible portion on each end of the rigid portion by a transition section in which the rigidity gradually decreases as the distance from the rigid portion increases. While Lam et al recognize that a planar annuloplasty ring fails to conform to the structure of the portions of the heart proximate the mitral valve, the Lam et al structure does not provide for complete conformation to varying orientations and configurations of the heart. While some conformation is permitted, the rigid structure and semi-rigid transition zones of Lam et al, referred to as being a selectively flexible ring, forces the tissue to conform in very large part to the configuration of the annuloplasty ring. It is an object of this invention to provide an annuloplasty ring that differs structurally and functionally from the Lam et al ring in that the ring is substantially planar, is adaptable to being sutured to generally annularly configured heart tissues in a generally planar configuration and to configuring to the heart tissue structure, and which provides distinct hinge-like structures at the end of a stiffener, rather than the gradually less-stiff transition, i.e. selectively stiff, structure provided by Lam et al.

Angell, U.S. Pat. No. 4,042,979, describes a partially rigid annuloplasty ring that comprises drawstring means in the form of a ribbon that is quite large relative to the ring, stiffener, and other structures and which is disposed closely adjacent the outer periphery of the ring and, thus, presents a difficulty in suturing the ring to the heart tissue in that the surgeon must avoid suturing the ribbon to the tissue. The ribbon is disposed adjacent the outer periphery of the Angell annuloplasty ring causing the ring to gather in bunched masses of irregular configuration when the ring is contracted. In addition, the rigid member of the Angell ring is secured only to the ribbon and both the ribbon and the rigid member are free to float within the ring resulting in an uncertainty as to the precise disposition of the rigid member in the ring and, consequently, an uncertainty in precise positioning of the rigid member relative to the heart annulus. It is another object of this invention to provide a ring which fixes the rigid member in the ring, marks specific locations on the ring for orienting the same and also provides drawstrings that are secured away from the outer periphery of the annuloplasty ring thereby avoiding interference in suturing and bunching or gathering of the ring upon contraction.

Suture rings of many forms are used to secure heart valve prostheses. Various forms of suture rings are depicted or described in the following U.S. Pat. Nos.: 3,534,411, 3,491, 376, 4,263,680, 5,104,406, 4,888,009, 4,865,600, 4,702,250, 4,477,930, and 4,451,936. It is an object of this invention to provide a suture ring suitable for use on heart valve prosthetic devices and the like for securing such devices in the heart or other annular tissue.

SUMMARY OF THE INVENTION

This invention relates to adjustable and flexible atrioventricular annuloplasty rings containing circumferential radiopaque markers with mitral and tricuspid valve variations specific to their varying requirements. Certain of the features of the invention are adaptable for use in manufacturing suture rings for securing heart valve prostheses in the appropriate location in the heart. A variant of the ring for use in the mitral region incorporates a curved framework in the anterior segment. The framework member is to maintain the intratrigonal and anterior leaflet distance during implantation. It is curved to prevent aortic outflow tract obstruction. Two or more pairs of drawstrings allow adjustment of four segments of the posterior portion of the mitral valve annulus. The variant of the ring for use in the tricuspid region incorporates a single drawstring to allow adjustment of the posterior left and right segment of ring at implantation. The flexible contractile body of the ring common to both variants is of a biocompatible cloth, preferably of a braided polyethertetraphylate tubular material, joined and folded in a particular manner that produces a eight walled body. The body is substantially oval in cross-section. The use of a braided material allows the ring the ability to contract under the action of the drawstrings without bunching.

Objectives of this invention include providing flexible, adjustable annuloplasty rings specific for use in mitral and tricuspid valve repair, providing an annuloplasty ring that may be adjusted in the required segments of the annulus, providing a mitral annuloplasty ring in which the intertrigonal distance and anterior segment is maintained during implantation.

Other objectives include providing an annuloplasty ring that may be adjusted in diameter by means of internal drawstrings during implantation to eliminate or minimize valvular regurgitation, providing an annuloplasty ring that in preferred embodiments the drawstring tie knots do not lie in the main blood flow path, providing an annuloplasty ring that will allow the surgeon to correct certain technical errors that might have occurred during implantation, providing a mitral annuloplasty ring that is flexible (in an undulating manner) so as to follow the change in shape of the mitral annulus, in the plane of the annulus, and providing a mitral annuloplasty ring that is flexible about the posterior portion of its circumference, and that prevents restriction of the left ventricular outflow tract.

Further objectives of the invention include providing a mitral annuloplasty ring that is capable of selective adjustable restriction in the posterior leaflet segments, providing a tricuspid annuloplasty ring that is capable of adjustable restriction in the posterior leaflet segment, providing an annuloplasty ring that is technically easy to use, providing an annuloplasty ring that is capable of being implanted and adjusted in a relatively short time, and providing an annuloplasty ring that is radiopaque around its entire circumference.

Other objectives include providing a suture ring that can be securely fastened to a heart valve or other annular prosthetic device for permitting the device to be sewn to tissue, and provide methods of manufacturing rings for the aforesaid and other purposes.

In one facet, the invention is embodied in a suture ring for use in surgery for securing a prosthesis in or adjacent to an annular organ structure or stabilizing or shaping a generally annular organ portion comprising, in combination: an elongate braided biocompatible ribbon having ends, elongate edges and a central portion, the lateral cross-section of the ribbon generally defining a V-shape, the edges extending outwardly from the center, means securing the respective ends of the ribbon together thereby configuring the ribbon generally into an annulus, the central portion defining the internal periphery of the annulus, the edges extending outwardly from said internal periphery; at least one drawstring extending around at least a portion of the annulus and through the ribbon selectively to decrease the diameter of the internal periphery of the annulus, the drawstring being disposed adjacent said center, the edges extending outwardly from the drawstring; and means securing the edges of the ribbon together, the edges of the ribbon defining the external annulus periphery; the drawstring and ribbon-like member being so constructed and configured that when the drawstring is drawn the internal diameter of the annulus contracts and the width of the annulus increases thereby substantially preventing the ribbon-like member from gathering into irregular clumps as the internal diameter of the annulus contracts.

In another facet the invention is suture ring for use in surgery for securing a prosthesis in or adjacent to an annular organ structure or stabilizing or shaping a generally annular organ portion comprising, in combination: biocompatible braided fabric tube defining an annulus, one portion of the tube defining an interior periphery of the annulus and a second portion of the tube defining an exterior periphery of the annulus; and at least one drawstring extending around at least a portion of the annulus and through the tube selectively to decrease the diameter of the internal periphery of the annulus, the drawstring being disposed in the tube adjacent the portion of the tube that defines the interior periphery, the portion of the tube defining the exterior periphery of the annulus being free of drawstrings for being sewn to the organ structure; the drawstring and tube being so constructed and configured that when the draw-string is drawn the internal diameter of the annulus contracts and the width of the annulus increases thereby substantially preventing the fabric of the tube from gathering into irregular clumps as the internal diameter of the annulus contracts.

In another facet the suture ring comprises biocompatible braided fabric tube defining an annulus, one portion of the tube defining an interior periphery of the annulus and a second portion of the tube defining an exterior periphery of the annulus; and at least two radiopaque thread segments lying side by side and extending around at least a portion of the annulus for permitting locating of the suture ring by x-radiation, the radiopaque thread being disposed in the tube intermediate the portion of the tube that defines the interior periphery and the portion of the tube defining the exterior periphery of the annulus for permitting the tube to be sewn through with a needle without interference.

The suture ring comprises, in one embodiment, a single length of tubing comprising braided biocompatible fibers, said tubing having first and second ends; one half of said tubing lying inside the other half of said tubing thereby forming a tube one half the length of said tubing, said tube having third and fourth ends and having an inner tubing wall and an outer tubing wall; means securing the first and second ends of the tubing together to form an end-to-end tubing joint, the end-to-end tubing joint being so constructed and positioned as to comprise a portion of inner tubing wall spaced from the ends of said double walled tube; means securing the third and fourth ends of the tube together to form said tube into an annulus.

In another embodiment, the suture ring comprises an annulus formed of tubing comprising braided biocompatible walls defining an inner annular periphery and an outer annular periphery; drawstring means extending through the wall of the tubing and inside the tubing around and proximate to at least a portion of the inner annular periphery of the annulus; and at least two colored marker sutures sewn into the tubing defining respective portions of the annulus to be sutured, when used, adjacent respective portions of the annular organ structure.

In yet another embodiment the suture ring comprises an annulus formed of tubing comprising braided biocompatible walls defining an inner annular periphery and an outer annular periphery; drawstring means comprising a plurality of drawstrings extending through the wall of the tubing, each drawstring extending inside the tubing around and proximate to at least a portion of the inner annular periphery of the annulus, the respective drawstrings defining respective portions of the annulus to be sutured to respective portions of the annular organ structure, the drawstrings being so constructed and configured with respect to the annulus as to permit the user to pull and tie each pair of drawstrings independently of each other pair of drawstrings for contracting the annulus only in the portion of the annulus defined by the respective drawstring. The respective pairs of drawstrings may be colored differently from one another to permit visual identification of each respective pair of drawstrings.

The invention is also embodied in an annuloplasty ring for use in repairing a human heart valve annulus, said ring having an inner annular periphery and an outer annular periphery and, between said peripheries, a first face constructed and configured to lie, when in use, against the annulus defined by the tissue surrounding a human tricuspid heart valve, and a second face opposite the first face, the annuloplasty ring comprising a flexible contractible portion, and at least one pair of drawstrings for contracting said contractible portion, said drawstrings exiting the first face of the ring lying against the tissue annulus.

The annuloplasty ring may have an inner annular periphery and an outer annular periphery constructed and adapted for being sutured to the human heart tissue and, lying between said peripheries, a first face constructed and configured to lie, when in use, against the annulus defined by the tissue surrounding a human tricuspid heart valve, and a second face opposite the first face, the annuloplasty ring comprising a flexible contractible portion, and at least one pair of drawstrings for contracting said contractible portion, said drawstrings exiting the first face proximate the inner annulary periphery for ring lying against the tissue annulus and being spaced from the outer annulary periphery.

The annuloplasty ring may be specifically for use in repairing a human mitral heart valve having an anterior segment and a right and left posterior segments. The ring comprises, in this embodiment, a braided fabric tube, means connecting the ends of the tube to thereby form the tube generally into an annulus and a stiffener wire extending substantially the length of the anterior segment, the stiffener wire having first and second ends, said ends being configured to form loops on the respective ends thereof. A first string the ends of which extend outwardly through the tube walls at first and second points respectively is provided. The first and second points are spaced from the first and second ends of the wire. The string extends inside the tube a point adjacent an end of the tube, thence around the tube, thence inwardly through the walls proximate the said end of the wire, thence through the loop in said end of the wire, thence outwardly through the walls, thence around the first string outside the tube, thence inwardly through the walls and over the first string, forming a knot to secure said end of the wire to the tube and to the first string to the first end of the wire, and thence into the tube and along the tube. At the second end of the tube, the knot is repeated from the direction of the wire with or without variation, e.g. reversal, in mirror image, etc. From the second end of the wire the string extends along the inside of the tube a second distance and thence outwardly through the tube wall at a second point said second distance from the second end of the wire, a first end of the first string extending out of the tube wall proximate the first point, the second end of the first string extending out of the wall proximate the second point. A second string extends from outside the annulus proximate a third point, through the tube away from the first end of the wire toward the second point, outwardly through the tube wall and inwardly through the tube wall proximate a fourth point to secure the second string proximate said fourth point, along the inside of the tube to proximate a fifth point, and thence through the tube wall, a first end of the second string extending out of the tube wall proximate the third point, the second end of the second string extending out of the tube wall proximate the fifth point. The third point may be adjacent the first point and the fifth point may be adjacent the second point, the second string form a knot at the fourth point if desired, and the first ends of the respective strings comprise a first pair of drawstrings for permitting contraction of the annulus between the first end of the wire and the first point and between the first point and the third point, respectively and the second ends of the respective strings comprise a second pair of drawstrings for permitting contraction of the annulus between the second end of the wire and the second point and between the second point and the third point, respectively.

One or more strings may be provided extending from outside the annulus proximate said first point, through the tube away from the first end of the wire toward the second point, outwardly through the tube wall and inwardly through the tube wall proximate a third point, that may, if desired, be approximately equidistant from the first and second ends of the wire, to secure the second string proximate said third point, along the inside of the tube to proximate the second point, and thence through the tube wall, a first end of the second string extending out of the tube wall proximate the first point, the second end of the second string extending out of the tube wall proximate the second point; the first ends of the respective strings comprising a first pair of drawstrings for permitting contraction of the annulus between the first end of the wire and the first point and between the first point and the third point, respectively; the second ends of the respective strings comprising a second pair of drawstrings for permitting contraction of the annulus between the second end of the wire and the second point and between the second point and the third point, respectively. The second drawstring need not permit contraction of the entire distance between the first and third and/or second and third points, respectively. If, as is clearly contemplated by the invention, a third drawstring is used the same result is achieved with substantially the same structure in the same way. Indeed, the drawstrings my be embodied in a series of shorter drawstrings. It will be understood, of course, that the greater contraction normally occurs between the first and second points lying opposite the portion wherein the stiffener lies. Thus, while a minimum of two drawstrings are required to obtain optimum functional performance, any number additional drawstrings would be equivalent in that the same contraction can be obtained in the same way, except in shorter segments of the annuloplasty ring.

The wire is preferably polished on all surfaces, the ends thereof are radiused and wherein the loops are formed without denting the wire in the portions thereof that lie adjacent the ends of the wire.

More generally, the invention may be a suture ring for use in surgery for securing a prosthesis in or adjacent to an annular organ structure or stabilizing or shaping a generally annular organ portion comprising, in combination: an annulus formed of tubing comprising braided biocompatible walls defining an inner annular periphery and an outer annular periphery; drawstrings extending through the wall of the tubing and inside the tubing around and proximate to at least a portion of the inner annular periphery of the annulus; and stitching extending through the walls of the tube around the annulus fixing the drawstrings proximate the inner annular periphery; the annulus and drawstrings being so constructed and configured that when the drawstrings are tied the inner annulus contracts and the distance between the inner and outer peripheries increases thereby substantially preventing gathering of the tubing.

One facet of the invention is embodied in a stiffener wire for a mitral annuloplasty ring comprising a biocompatible wire in the configuration of an arc substantially defined by a radius equal to the radius of the mitral valve for which the annuloplasty ring is intended for use, the wire forming the arc having an inner periphery and an outer periphery, the respective ends of the wire being constructed to define at each end a generally circular passage through a loop substantially tangential with the outer periphery of the wire, the wire being smooth, free of sharp structures or edges, and free of indentations.

As an annuloplasty ring for use in repairing a human mitral heart valve having an anterior segment and a right and left posterior segments, the ring may have a first face constructed and configured to lie, when in use, against the annulus defined by the tissue surrounding a human heart valve, and a second face opposite the first face, the annuloplasty ring comprising said ring having a first face constructed and configured to lie, when in use, against the annulus defined by the tissue surrounding a human heart valve, and a second face opposite the first face, the annuloplasty ring comprising: a first portion constructed and configured to form a curved member that encompasses substantially the whole of the anterior segment of the human valve annulus; a second portion constructed and configured to form a flexible, contractible member that encompasses substantially the whole of the right and left posterior segments of the human mitral valve annulus; and means in the ring for selectively contracting, independently of one another, either the right posterior segment or the left posterior segment, or both posterior segments; the second portion being so constructed and configured and connected respectively at first and second ends thereof to first and second ends, respectively, of the first portion, the first portion being relatively substantially more rigid that the second portion, the first and second ends of the second portion being so constructed and configured as to permit hinging movement of the second portion relative to the first portion adjacent the ends of the first portion to permit the ring to conform to the human mitral valve annulus.

The invention may be in the form of an annuloplasty ring for use in repairing a human mitral heart valve having an anterior segment and a right and left posterior segments, said ring having a first face constructed and configured to lie, when in use, against the annulus defined by the tissue surrounding a human heart valve, and a second face opposite the first face, the annuloplasty ring comprising: a first portion constructed and configured to form a curved member that encompasses substantially the whole of the anterior segment of the human valve annulus; a second portion constructed and configured to form a flexible, contractible member that encompasses substantially the whole of the right and left posterior segments of the human mitral valve annulus; the first and second portions together constructed and configured such that the first and second portions, respectively, lie generally in first and second planes; and means in the ring for selectively contracting, independently of one another, the right posterior segment proximate one end of the curved member, the right posterior segment distal from the said one end of the curved member, the left posterior segment proximate the other end of the curved member, or the left posterior segment distal from the said one end of the curved member. The second portion may be adapted to lie adjacent the left posterior segment is contractible by means of a first pair of drawstrings and the second portion that is adapted to lie adjacent the right posterior segment is contractible by means of a second pair of drawstrings. The drawstrings preferably exit the first face of the ring that is constructed and configured to lie against the tissue annulus.

The annuloplasty ring of this invention is, in one form adapted for use in repairing a human mitral heart valve having an anterior segment and a right and left posterior segments, said ring having a first face constructed and configured to lie, when in use, against the annulus defined by the tissue surrounding a human heart valve, and a second face opposite the first face, the annuloplasty ring comprising: a first portion constructed and configured to form a curved member that encompasses substantially the whole of the anterior segment of the human valve annulus; and a second portion constructed and configured to form a flexible, contractible member that encompasses substantially the whole of the right and left posterior segments of the human mitral valve annulus; and at least one pair of drawstrings in the second portion, said portion being contractible by means of said drawstrings, said drawstrings exiting the first face of the ring intended to lie against the tissue annulus.

The annuloplasty ring may, however, be adapted for use in repairing a human tricuspid heart valve, said ring having a first face constructed and configured to lie, when in use, against the annulus defined by the tissue surrounding a human tricuspid heart valve, and a second face opposite the first face, the annuloplasty ring comprising a flexible contractible portion, and at least one pair of drawstrings for contracting said contractible portion, said drawstrings exiting the first face of the ring lying against the tissue annulus.

The tricuspid annuloplasty ring embodiment may comprise an annulus comprised of multi-layers of braided tube formed from a single length of tubular braid that is invaginated to form a double walled tube having first and second ends and inner and outer walls, a roll over fold formed at one end thereof, and the two cut ends formed at the other end thereof, the two walls of the tube being heat sealed together at the cut ends. In the preferred manufacture of the invention, the tubing is cut and the two cut ends are sealed together in the same operation by melting the polymer of which the tubing is formed. The tube is then rolled so that the heat seal line lies substantially centrally in the inner wall of the tube and is then heat set into a "V" configuration to produces an eight wall flexible contractile member.

The invention is embodied in a method of manufacturing an annuloplasty or suture ring comprising the steps of: invaginating tubing braided of meltable, heat setable polymer fibers to form a tube of an outer layer and an inner layer of tubing, a first end of the tube thus formed being defined by an annular, inward fold of the tubing from the outer layer to the inner layer; forming a second end of the tube by melting the inner and outer layers of tubing to fuse said layers together in an annular seal between said layers; and sliding said layers relative to each other defined new ends of annular, inward folds of tubing and to space the annular seal distal from and between the newly formed ends inside the outer layer of the tube. The method may further comprise heat setting the thus formed tube into a lateral V configuration having a center heat set crease comprising four layers of tubing.

More generally, the invention may be in the form of a suturable strip suitable for use in the manufacture of prosthetic devices comprising an elongate tube formed of an outer layer and at least one inner layer of heat set braided polymeric fabric, the ends of the suturable strip being inward annular folds of said fabric, the tube being heat set to define a ribbon the center of which is a heat set bend comprising at least four layers of such fabric defining a lateral cross-section of the strip into a generally V-shaped configuration, the outer layer of fabric forming said strip being free of joinders of the fabric.

In a specific application, one facet of the invention is embodied in a stiffener wire for use in annuloplasty rings comprising flexure fatigue resistant biocompatible corrosion resistant metal wire the central majority of the wire being formed into an arc, the respective ends of the wire forming a loop externally tangential to said arc, the ends of the wire lying immediately adjacent portions of the wire spaced from the ends, the loops and the arcuate central majority lying in the same plane, the ends of the wire and all surfaces of the wire being free of sharp structures, the portions of the wire immediately adjacent the ends of the wire being free of distortion or reduction in diameter.

Other objectives and advantages of this invention will be more apparent from the detailed description of the device which follows.

BRIEF DESCRIPTION OF THE DRAWINGS

The present invention may be better understood and the advantages will become apparent to those skilled in the art by reference to the accompanying drawings, wherein like reference numerals refer to like elements in the several figures, and wherein:

FIGS. 12C and 12D depict the stiffener wire in a further stage of manufacture, the loops and the wire lying in the same plane.

FIGS. 17A, 17B, 17C, 17D and 17E depict the tube at various stages during the formation of the invaginated tube used in forming the ring, FIG. 17E being a cross-sectional view of the tube as depicted in FIG. 17D, the section taken along lines 17E—17E in the direction of the arrows.

FIG. 18 is an exploded perspective view of the jig fixing the invaginated tube into a V configuration for being heat set in that V configuration.

FIG. 19 is a perspective view of the heat set V-shaped invaginated tube before being formed into an annulus.

DESCRIPTION OF THE PREFERRED EMBODIMENTS

Figure 1:
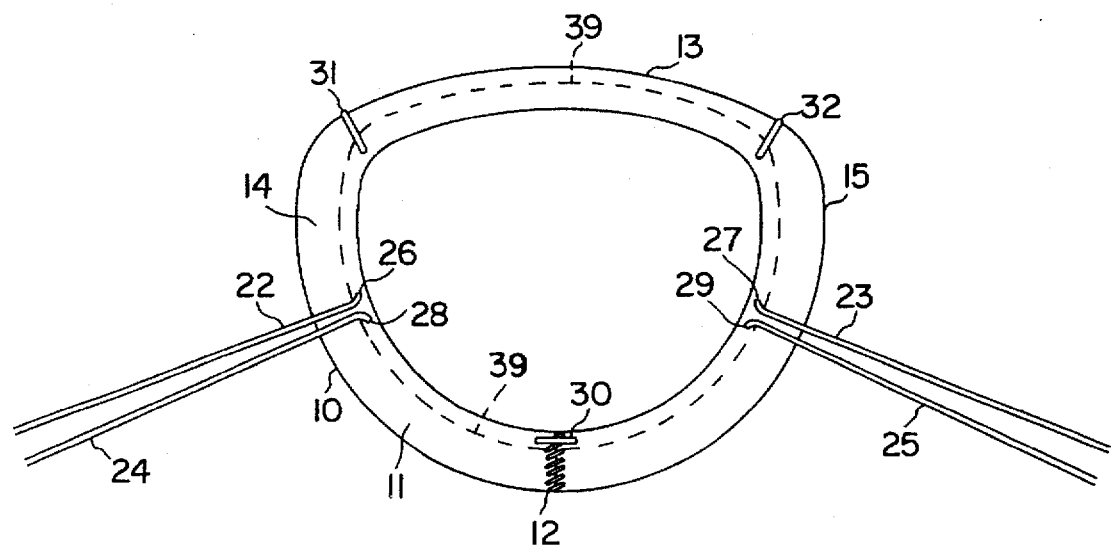
FIG. 1 depicts a plan view from the tissue annulus aspect of the preferred embodiment of the ring intended for the mitral valve.

The following description of the preferred embodiments of the invention are exemplary, rather than limiting, and many variations and adaptations are within the scope of the invention.

In one facet, the invention is directed to adjustable and flexible atrio-ventricular annuloplasty rings containing circumferential radiopaque markers with one preferred embodiment for use in mitral valve and a second preferred embodiment for use in tricuspid valve repair. Adjustment of the ring diameter is achieved by means of internal drawstrings. To avoid the presence of a bulky knot on the inflow aspect of the rings, the drawstring exit points are preferably located on the face of the ring which lies adjacent to the tissue annulus. Hence, when the drawstrings are tightened and pairing ends are tied together, the knots are formed between the annulus and the ring, out of the direct blood flow.

In the preferred embodiment of the invention intended for use in the mitral valve, the flexible, contractile portion of the prosthesis is formed to fit about the base of the posterior leaflet of the valve. A plurality of pairs of drawstrings are located in the posterior segment of the ring to allow adjustment of segments of the posterior portion of the mitral valve annulus. A curved framework member located in the anterior portion of the prosthesis is to maintain the natural geometry of the anterior segment during implantation. It is shaped to follow a curved path on an inclined plane on the sub aortic curtain above the so called annulus of the anterior leaflet. Colored trigone markers in the anterior segment are used as sizing and implanting guides. When the mitral annuloplasty ring is secured into position about the valve, any or all of the drawstrings located in the posterior segment of the valve annulus may be tightened if required to halt or minimize any residual valvular insufficiency. Drawstring tightening may be made individually or together in pairs to minimize any remaining insufficiency. This fine tuning capability allows a larger, rather than a smaller ring to be implanted and then the size optimally reduced.

In the preferred embodiment of the invention intended for use in the tricuspid valve, the prosthesis is flexible around its circumference and is formed to fit about the base of the valve leaflets. A contractible portion of the prosthesis is formed to fit about a substantial portion of the base of the posterior segment, and may extend into a insubstantial portion of the base of the anterior segment of the valve annulus. This contractible segment incorporates a pair of drawstrings to allow adjustment of a substantial segment of posterior annulus and an insubstantial segment of the anterior annulus at implantation. When the tricuspid variant is secured into position about the valve, the drawstrings located in the posterior segment of the valve annulus may be tightened if required. Tightening may be individually or in pairs to minimize any remaining insufficiency. This fine tubing capability allows a larger, rather than a smaller ring to be implanted and then the size optimally reduced.

The flexible contractible body of the ring common to both variants is of a biocompatible cloth, preferably of a braided polyethertetraphylate tubular material. During construction of the ring, the tubular braid is cut to length and invaginated to form a double walled tube having a roll over fold at one end, and the two cut ends at the other. The two walls of the tube are heat sealed (welded) together close to the two cut ends and at an appropriate distance from the folded end using a heated knife. This heat seal forms a circumferential weld around the tube. The tube is then rolled so that the weld line will lie substantially centrally in the inner wall of the tube. The tube is then heat set into a "V" configuration. This configuration produces an eight walled flexible contractile member when the annuloplasty ring is completed. Two of the many steps in the completion of the ring include the sewing of the folded ends together to form a radial seam, and sewing of the apices of the "V" together to form a circumferential seam. Various components, such as drawstrings, stiffener and radiopaque markers are conveniently placed within and/or sewn in the "V" form before the circumferential seam is completed. This construction method produces an annuloplasty ring that is relatively simple to manufacture, yet contains drawstrings to provide adjustability, radiopaque markers for postoperative assessment, and a semi-flexible member in the anterior portion of the mitral variant to maintain the natural geometry of the intratrigonal and anterior leaflet distance. At the same time it provides adequate strength and flexibility, yet permits a low needle penetration force for convenience of implantation. A particular advantage of this construction is that there are no portions of the textile material that might fray, and that the weld line is so placed within the ring is both inconspicuous and not subject to undue stresses. The body is substantially oval in cross-section.

Figure 2:
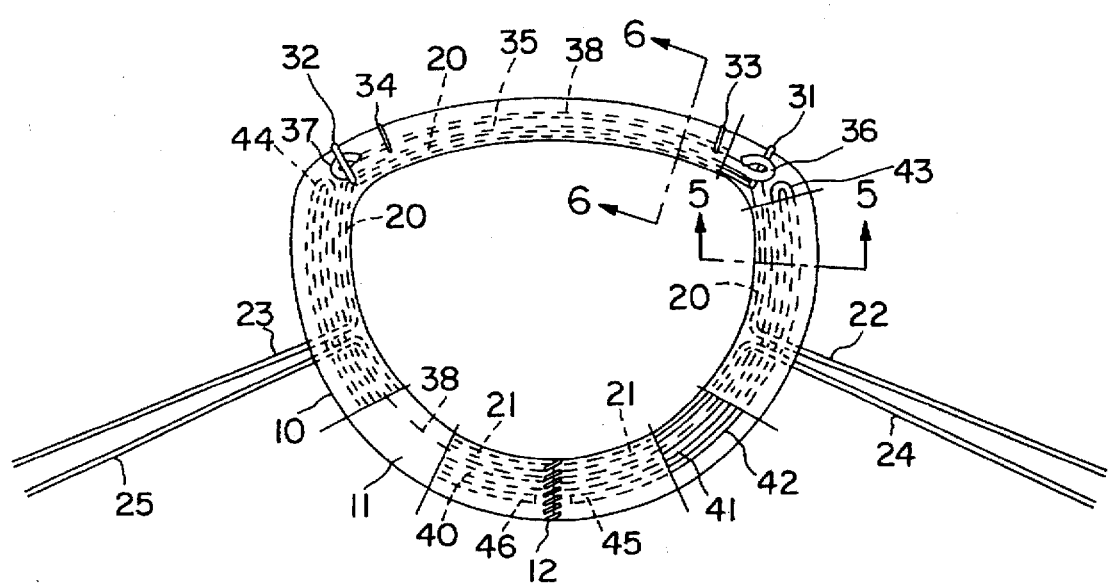
FIG. 2 depicts a plan view from the atrial aspect of the preferred embodiment of the ring intended for the mitral valve, portions depicting the internal structure of the ring.
Figure 3:
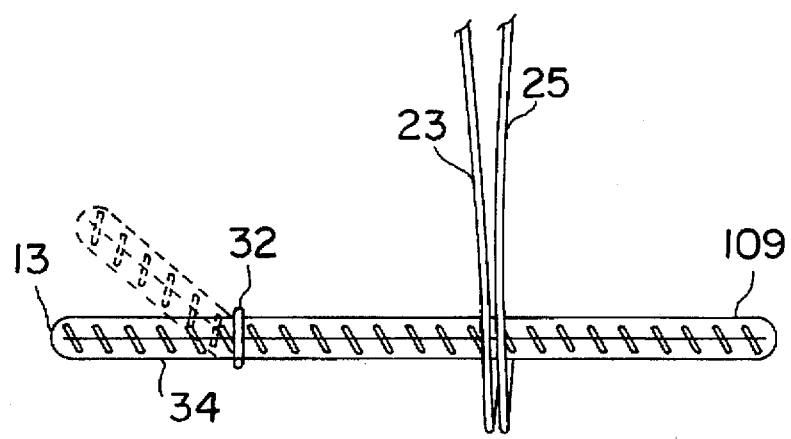
FIG. 3 depicts a side view of the ring intended for mitral valve repair, a hinged, bent bi-planar configuration being shown in broken lines.
Figure 4A:
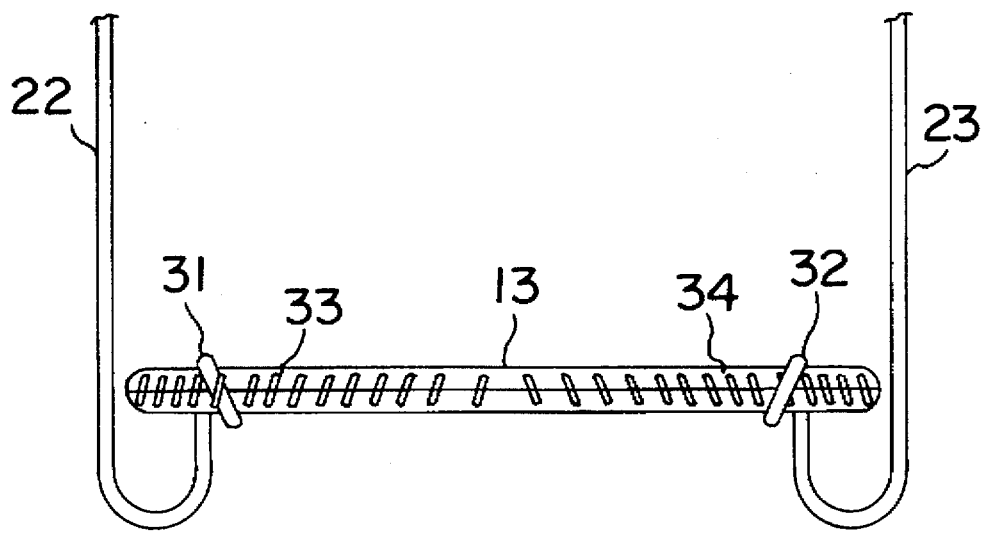
FIG. 4A depicts an end view of the preferred embodiment of the ring intended for mitral valve repair.
Figure 4B:
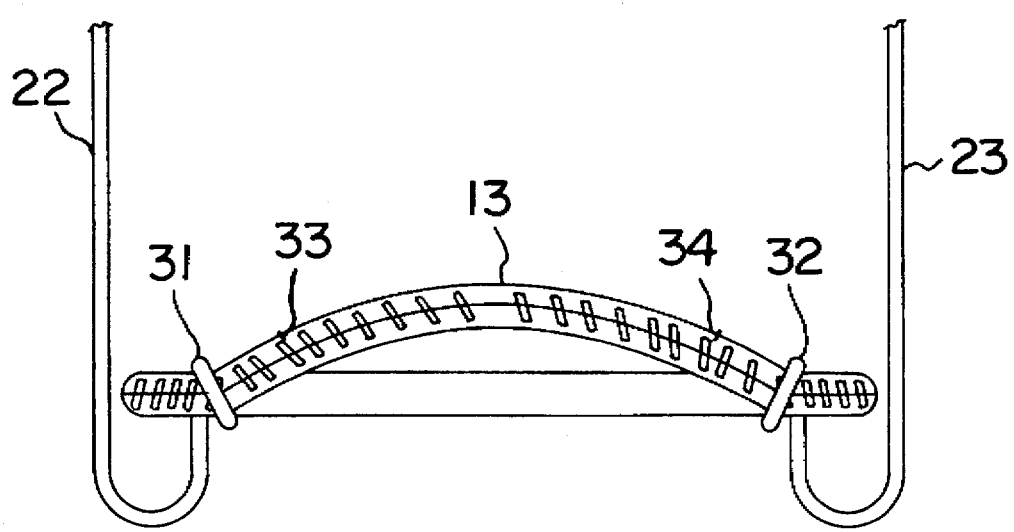
FIG. 4B depicts an end view of the preferred embodiment of the ring intended for mitral valve repair, the rigid portion being bent at the hinge portions to lie outside the main plane of the ring.
Figure 5:
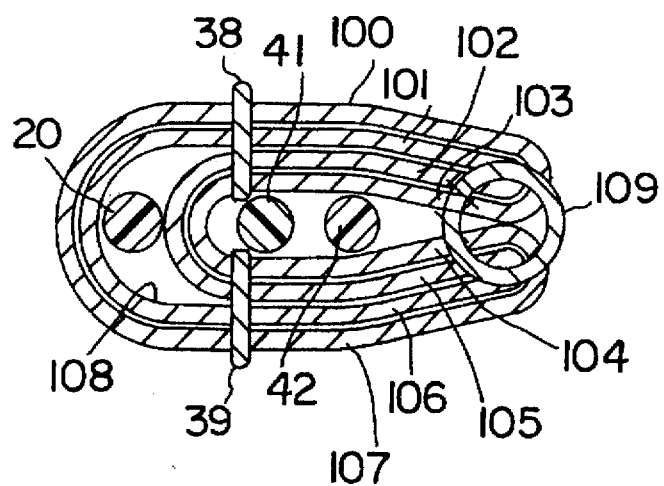
FIG. 5 depicts a cross-sectional view taken along line 5—5 of FIG. 2.
Figure 6:
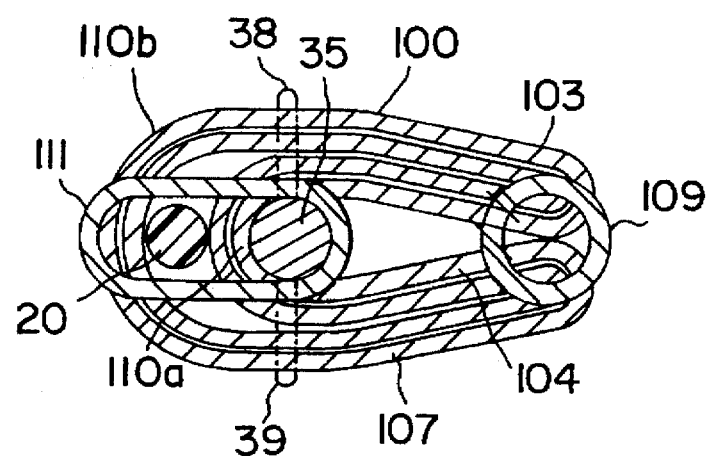
FIG. 6 depicts a cross-sectional view taken along line 6—6 of FIG. 2.

Referring to the drawings wherein like numerals indicate like elements there is shown in FIG. 1 and FIG. 2 plan views (from the annulus and atrium aspects respectively) of the preferred embodiment of a flexible, adjustable annuloplasty ring intended for the mitral valve designated as 10. FIG. 3 shows a side view and FIG. 4 shows an end view of the preferred embodiment of the variant of the ring intended for the mitral valve. FIG. 5 shows a cross-sectional view taken along line 5—5 of FIG. 2. FIG. 6 shows a cross-sectional view taken along line 6—6 of FIG. 2.

The device is composed of a tubular body of textile nature 11, which has its folded ends sewn together at seam 12 to form a ring. The ring has three segments, the anterior segment 13, the right posterior segment 14, and the left posterior segment 15. In the interior of tubular body 11 are provided filiform strings 20, 21, which have external portions 22, 23, 24, 25. These strings, which are preferably of a braided polyester surgical suture, emerge from the annulus face of the ring at exit points 26, 27, 28, 29 respectively. The distance between exit points 26 and 28 are approximately 3 mm. The distance between exit points 27 and 29 is similar.

The strings are anchored to the ring at points 30, 31, and 32. Points 33 and 34 are colored markers sewn onto the upper (atrial) surface of the ring that are intended as guides for implantation. These points are intended to lie adjacent to the right and left fibrous trigones of the mitral annulus. Also at implantation, point 31 will approximately correspond to the junction of the anterior leaflet and the right commissural leaflet of the mitral annulus. Point 32 will approximately correspond to the junction of the anterior leaflet and the left commissural leaflet. An internal curved flexible stiffener member 35 spans the area corresponding to the anterior segment of the mitral annulus from points 31 to 32, and has a closed loops 36, 37 at its ends. Drawstring 20 is passed through these loops and through the walls of body 11 to form part of the anchor knots at 31 and 32. Drawstring 21 is passed through the walls of body 11 to lie externally for a short distance 30 and is tied internally to form the anchor knot laying under external portion 30.

The framework or stiffener member 35 is preferably of a biocompatible corrosion resistant metal wire with good flexure fatigue resistance such as carpenter MP35N alloy or Elgiloy.

Figure 13:
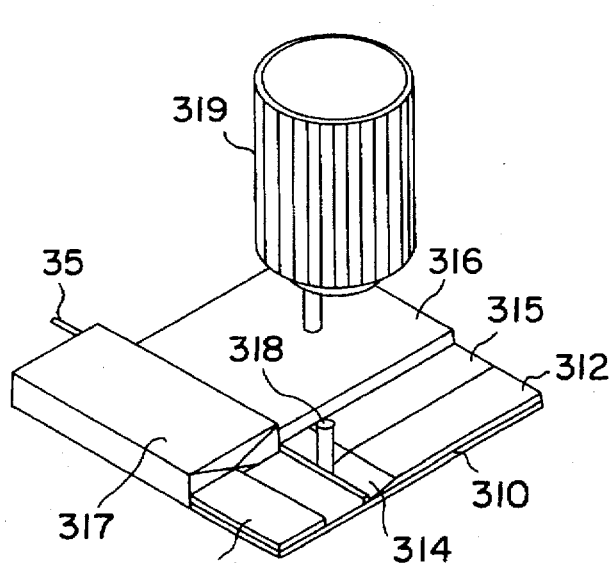
FIG. 13 is an exploded perspective view depicting a jig for forming the stiffener wire.
Figure 14A:
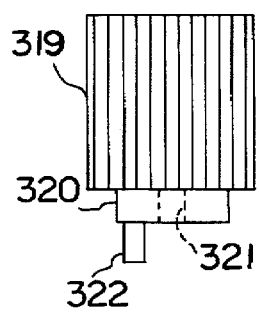
FIGS. 14A and 14B depict, respectively, a side elevational view and a bottom plan view of the bending tool of FIG. 13.
Figure 14B:
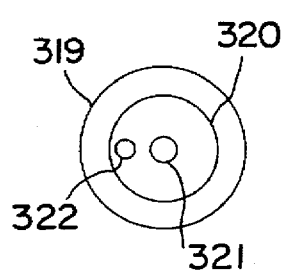

Reference is made briefly to FIG. 12 through 14. A wire 35 of the material described, e.g. Carpenter MP35N, 0.028" diameter, or equivalent, is first inspected. Next, the wire is cut to the desired length, with an abrasive saw, or an equivalent device, burnished to assure that it is smooth, and secured in a jig such as is depicted in FIG. 13. The jig comprises a base plate 310, a locking bar 311, a wedge plate 312 having an incline surface 313, and a support plate 314 are secured to the base plate. A lock plate 315 is secured to the support plate 314 and interacts with lock bar 316, that has a beveled corner 317 to receive and lock firmly in position the wire 35. The wire 35 extends to the edge of the base plate which serves as measure of the length of wire to be formed into a loop and lies adjacent a mandrel post 318 that is less than the diameter of the loop to be formed in the end of wire 35. A bending tool 319, comprising a knob capable of being gripped and turned, with a downwardly extending portion 320 having formed centrally therein an aperture 321 sized to slip snugly over mandrel post 318 and an engaging post 322 that is spaced from the aperture a distance slightly larger than the diameter of the wire 35. The bending tool is fitted over the mandrel post, the wire 35 being received between the mandrel post and the engaging post. The bending tool is turned thereby bending the wire 35 into a semihelical loop. It is necessary to bend the wire into a smaller loop than the ultimately desired loop because the wire rebounds slightly from its ultimately looped configuration. When the bending tool is removed, the wire, which has been burnished to assure that it is smooth, assumes the configuration shown in FIGS. 12A and 12B, with the loop, such as loop 36a or 37a, spiraling partially out of the plane of the wire. The end of the wire, e.g. 36b or 37b, which has been smoothly cut with an abrasive saw and rounded and burnished to remove all sharp edges, burrs, etc., is then bent downwardly, as shown in FIG. 12B so that the loops lie in the same plane as the wire, as shown in FIG. 12C and 12D, the ends lying closely adjacent the wire a short distance from the ends. The loop is bent to assure that the end of the wire, as bent, depicted in FIGS. 12A and 12B, does not overlap the portion of the wire to which is closely adjacent. When the loop is bent into the plane of the wire, the wire in that portion is not dented, distorted or deformed. As a final step, before final inspection, the stiffener 35 is burnished again to assure that it is perfectly smooth, free of indentations or deformations that may weaken it, and free of sharp edges or other structures that might abrade the fabric of the ring.

A colored demarcation suture line 38 on the upper (atrial) surface of the ring body indicates to the surgeon a line, outside of which the implanting sutures must be placed to avoid interference with the internal drawstrings or the stiffener member. A corresponding, but preferably uncolored, demarcation suture line 39 is situated on the lower (annulus)

surface of the ring body. A flexible radiopaque member 40, is contained within body 11, in the posterior region between drawstring anchor points 31 and 32. This member, in conjunction with metallic stiffener 35, forms a circumferential X-ray marker. Member 40 may conveniently be composed of a single continuous length of 0.020" diameter extruded silicone rubber impregnated with 55% Barium Sulfate and 6% Tungsten. Material of this composition and diameter is sufficiently radiopaque, but does not unduly impede the passage of the needles of the implanting sutures. It has elements 41, 42, "hairpin" bends 43, 44, and ends 45, 46. The "hairpin" bends 43, 44, lie adjacent to loops 36, 37 respectively, and ends 45, 46 lie adjacent to seam 12.

FIG. 5 shows a cross-sectional view taken along line 5—5 of FIG. 2. Cloth layers 100, 101, 102, 103, 104, 105, 106, 107 are formed from a singular tubular braided length of material folded and joined as previously described. The four cloth layers, when folded and heat set, form an upper (atrial) surface 100, and a lower surface 107 that will lie on the natural annulus. Colored demarcation stitch 38 passes from cloth layer 100, through layers 101, 102, 103 and hence back to layer 100. The second demarcation stitch 39, which is preferably uncolored (white), is similarly passed from cloth layer 107, through layers 106, 105, 104 and hence back to layer 107. Demarcation sutures 38, 39 passing through their respective cloth layers delineate channel 108 which contains drawstring 20 (or 21). Radiopaque marker member portions 41, 42 are enclosed between cloth layers 103, 104. A helical, continuous, circumferential sewn seam 109 joins cloth layers 100, 101, 102, 103 to corresponding cloth layers 107, 106, 105, 104.

FIG. 6 shows a cross-sectional view taken along line 6—6 of FIG. 2. Framework member 35 is retained along its length against the fold 110a of the cloth layer 103, 104 by a continuous helical thread 111, and/or by suture ties 38 and 39, for example. The fold 110a is a single layer of tubing lying innermost in the four-layer braided fabric construction, the exterior bend 110b forming the outermost layer of said four-layer construction.

Figure 7:
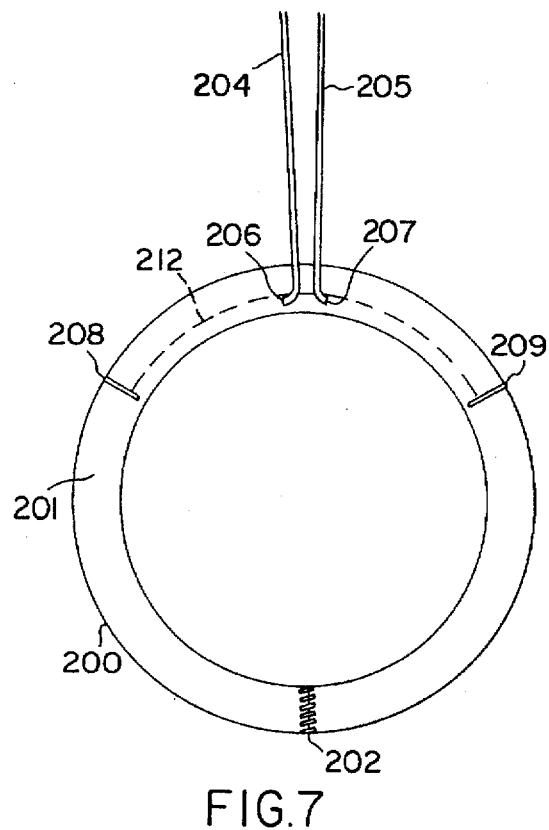
FIG. 7 depicts a plan view from the tissue annulus aspect of the preferred embodiment of the ring intended for the tricuspid valve.
Figure 8:
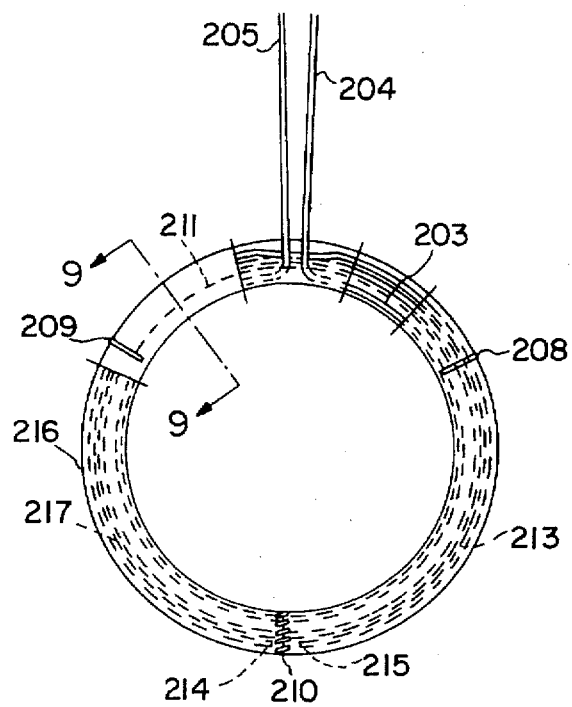
FIG. 8 depicts a plan view from the atrial aspect of the preferred embodiment of the ring intended for the tricuspid valve, portions depicting internal structure.
Figure 9:
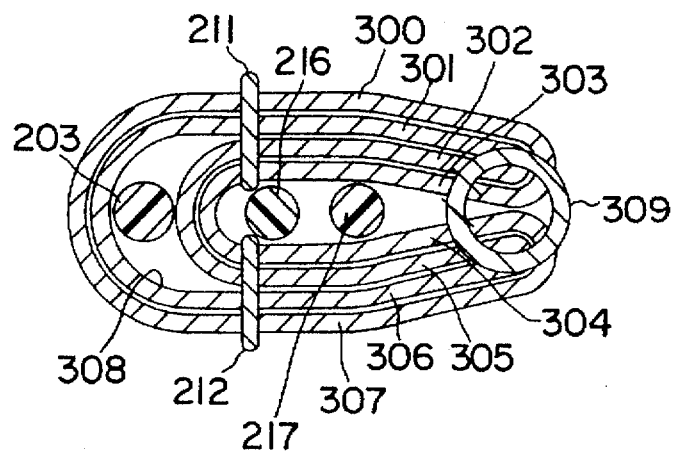
FIG. 9 shows a cross-sectional view taken along line 9—9 of FIG. 8.

FIG. 7 and FIG. 8 show plan views (from the annulus and atrial aspects respectively) of the preferred embodiment of a flexible, adjustable annuloplasty ring intended for the tricuspid valve designated as 200. FIG. 9 shows a cross-sectional view taken along line 9—9 of FIG. 8. The device is composed of a tubular body of textile nature 201, which has its folded ends sewn together at seam 202 to form a ring. In the interior of tubular body 201 is provided a filiform string 203 which has external portions 204, 205. This string, which is preferably of a braided polyester surgical suture, emerges from the annulus face of the ring at exit points 206, 207. The distance between exit points 206 and 207 is approximately 3 mm. The string also emerges from, passes around the body (208, 209) and reenters the body 201 at the drawstring anchor points. The string is anchored in the ring by internal looped knots adjacent to external loops 208, 209.

A colored marker 210 is sewn onto the upper (atrial) surface of the ring. This is a guide to the surgeon, indicating the point that should be positioned adjacent to the junction of the septal and anterior leaflet at implantation. A colored demarcation suture line 211 on the upper (atrial) surface of the ring body indicates to the surgeon a line, outside of which the implanting sutures must be placed to avoid interference with the adjustable segments of the internal drawstring 203. A corresponding, but preferably uncolored, demarcation suture line 212 is situated on the lower (annulus) surface of the ring. A flexible member 213, is contained within body 201. This member forms a circumferential radiopaque marker. It may conveniently be composed of a single length of 0.020" diameter extruded silicone rubber impregnated with 55% Barium Sulfate and 6% Tungsten. This member 213, having ends 214, 215 lying adjacent to seam 202 passes twice around the circumference of the ring to form concentric members 216, 217.

FIG. 9 shows a cross-sectional view taken along line 9—9 of FIG. 8. Cloth layers 300, 301, 302, 303, 304, 305, 306, 307 are formed from a singular tubular braided length of material folded and joined as previously described. The four layers, when folded and heat set, form an upper (atrial) surfaces 300, a lower surface 307 that will lie on the natural annulus. Colored demarcation stitch 211 passes from cloth layer 300, through layers 301, 302, 303 and hence back to layer 300. A second demarcation stitch 212, which is preferably white, is likewise passed between cloth layer 307, through layers 306, 305, 304 and hence back to layer 308. Demarcation sutures 211, 212 passing through their respective cloth layers delineate channel 308 which contains drawstring 203. Radiopaque marker member elements 216, 217 are enclosed between cloth layers 303, 304. A helical, continuous, circumferential sewn seam 309 retains cloth layers 300, 301, 306, 307 together.

Figure 15:
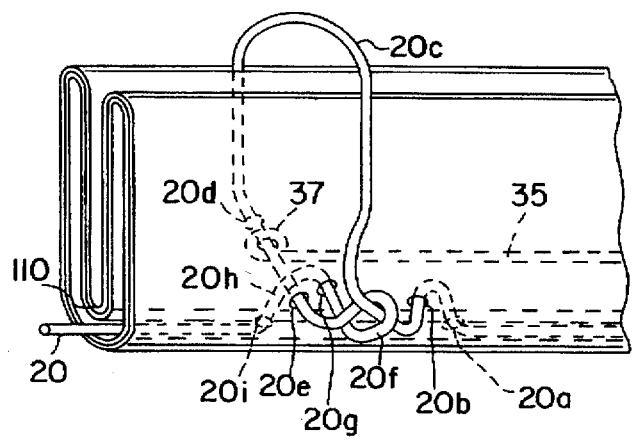
FIG. 15 depicts the tie of the drawstring to the stiffener wire before tightening the same into a knot.

In the embodiment of the annuloplasty ring specifically adapted for use in repairing a human mitral heart valve having an anterior segment and a right and left posterior segments a braided fabric tube is connected to form the tube generally into an annulus. The stiffener wire extending substantially the length of the anterior segment, the stiffener wire having first and second ends, said ends being configured to form loops on the respective ends thereof. As depicted in FIG. 15, a first string 20 extends from outside the annulus through the wall of the tube at a first point 20a a first distance from the first end of the wire into the tube. Adjacent the first end of the wire the string extends outwardly through the tube wall at 20c, through the four-layer wall at 20d, thence around the tube as indicated at 20e, thence inwardly through the four layers proximate the first end of the wire, 20f, thence through the loop 37 in said first end of the wire 35, thence outwardly through the walls, 20g, thence around the first string outside the tube, 20h, thence inwardly through the walls, 20i, and over the first string at again, 20j forming a knot to secure the string 20 and the first end loop 37 of the wire 35 to the tube proximate the first end of the wire. The string 20 then extends through the wall at 20k and along the length of the tube. At the second end of the tube, knot is repeated from the direction of the wire, i.e. a mirror-image of the arrangement just described is formed securing the other end of the wire and the string to the tube proximate the second end of the tube. As will be apparent, the securement just described can be accomplished from either direction, relative to the end of the wire, and may be the same or reversed, e.g. a mirror image knot, at the respective ends of the wire. Other knot securements may also be used. From the second end the string extends along the inside of the tube a second distance and thence outwardly through the tube wall at a second point said second distance from the second end of the wire, a first end of the first string extending out of the tube wall proximate the first point, the second end of the first string extending out of the wall proximate the second point 20b. The points 20d, 20g, and 20i may be coincident, i.e. a single hole may define all of these points.

One or more strings may be provided extending from outside the annulus proximate said first point, through the tube away from the first end of the wire toward the second point, outwardly through the tube wall and inwardly through the tube wall proximate a third point, that may, if desired, be approximately equidistant from the first and second ends of the wire, to secure the second string proximate said third point, along the inside of the tube to proximate the second point, and thence through the tube wall, a first end of the second string extending out of the tube wall proximate the first point, the second end of the second string extending out of the tube wall proximate the second point; the first ends of the respective strings comprising a first pair of drawstrings for permitting contraction of the annulus between the first end of the wire and the first point and between the first point and the third point, respectively; the second ends of the respective strings comprising a second pair of drawstrings for permitting contraction of the annulus between the second end of the wire and the second point and between the second point and the third point, respectively. The wire is preferably polished on all surfaces, the ends thereof are radiused and wherein the loops are formed without denting the wire in the portions thereof that lie adjacent the ends of the wire.

Figure 10:
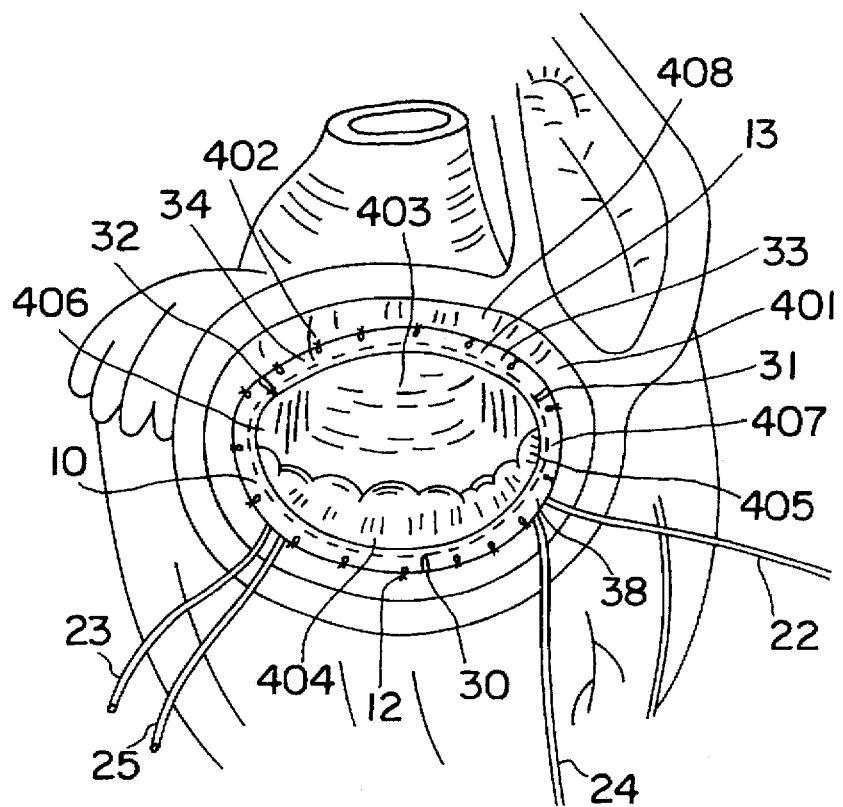
FIG. 10 is an isometric view of the preferred embodiment of the ring for mitral valve repair sewn onto the mitral annulus of the heart.

FIG. 10 shows an isometric view of the preferred embodiment of the ring for mitral valve repair sewn onto the mitral annulus of the heart (the left atrium is removed for clarity of illustration). The heart is shown during ventricular systole (i.e. the mitral valve is closed and the left ventricular outflow track is pressurized). The annuloplasty ring 10, is positioned such that colored markers 33, 34, are coincident to the right fibrous trigone 401 and left fibrous trigone 402 of the mitral valve apparatus. The anterior leaflet 403 is shown coapting to the posterior leaflet 404. Seam 12 will lie approximately at the midpoint posterior portion of the annulus. Drawstring anchor point 31 is located on the annulus approximately at the junction of the anterior leaflet and the right commissural leaflet, 405. Likewise, drawstring anchor point 32 is located on the annulus approximately at the junction of the anterior leaflet and the left commissural leaflet, 406.

The curved anterior portion of the ring 13 containing the internal curved framework member spans the anterior segment of the mitral annulus 403 from points 31 to 32. As manufactured, the plane of segment 13 lies in the same plane as the ring, as shown in solid lines in FIG. 3 and as depicted in FIG. 4A. The flexible ring forms a hinge immediately adjacent the ends of the framework member permitting the framework member to hinge or bend outside the plane of the ring up to an angle of approximately 85° relative to the plane of the remainder of the ring. Depending on the particular application of the ring, the framework may, during some periods of time, hinge such that the plane in which the framework lies at an angle typically of about 45° and up to 85° relative to the plane of the remainder of the ring. In some applications, the ring, including the framework portion, will lie substantially in the same plane. The angle, if any, in which the framework lies is not a function of the annuloplasty ring per se but rather of configuration of the heart, or other organ, to which the ring is applied and to the method the surgeon uses for applying the ring. A colored demarcation suture line 38 on the upper (atrial) surface of the ring body indicates to the surgeon a line, outside which the implanting sutures 407 must be placed to avoid interference with the internal drawstrings or the stiffener member. Numerous interrupted sutures 407, are used to fix annuloplasty ring to the mitral valve annulus and to the sub aortic curtain 408. External portions of the drawstrings 22, 23, 24, 25 may be tightened and tied to the adjoining drawstring to constrict the ring where required to correct or minimize valvular insufficiency. The act of drawing in either or both drawstrings 22, 24 and or 23, 25 will cause the ring to contract between the drawstring anchor points 30 and 31 or 30 and 32 respectively. The amount of contraction will depend upon how much each drawstring is tightened, and whether only one or all drawstrings are tightened. By such means the circumference of the annulus may be further reduced to correct or minimize any remaining valvular insufficiency following ring implantation. It is emphasized that, as to the present invention, there is no significance to the showing or one or two or three pairs of drawstrings, as any number of drawstrings are contemplated by this invention.

Figure 11:
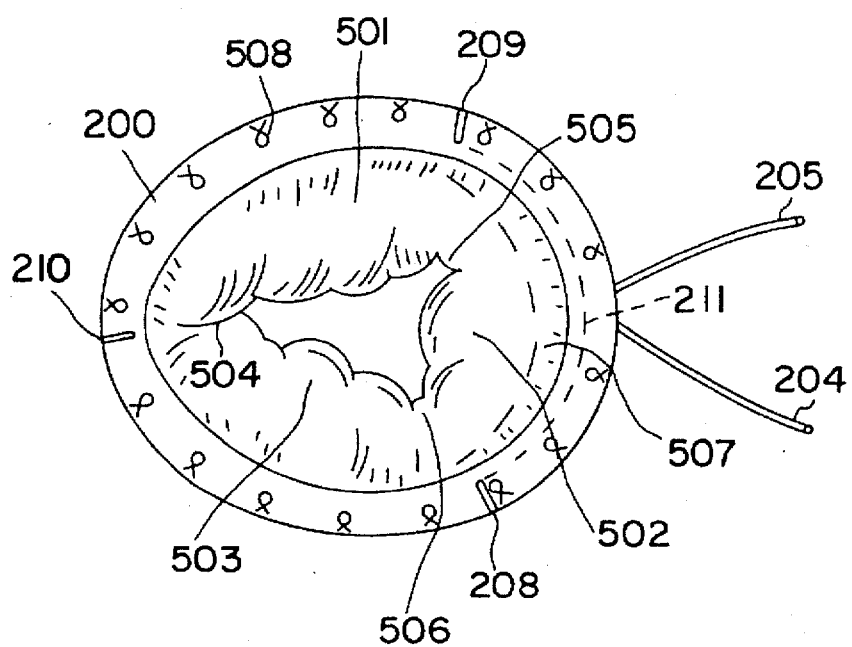
FIG. 11 is a plan view of the preferred embodiment of the ring for tricuspid valve repair sewn onto a typically enlarged tricuspid annulus and insufficient tricuspid valve of the heart.
Figure 12A:
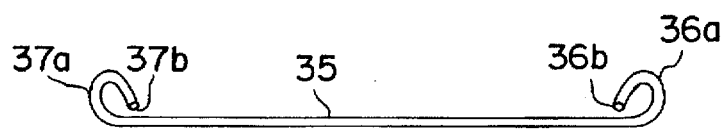
FIGS. 12A, 12B, 12C and 12D depict the stiffener wire used in the mitral valve, FIGS. 12A and 12B depicting the stiffener wire during manufacture, with the end loops partially formed.
Figure 12B:
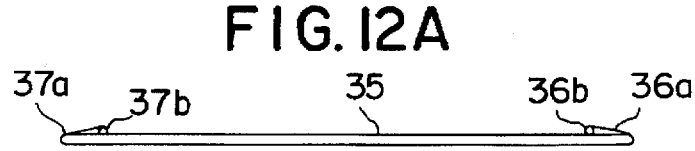
Figure 12C:
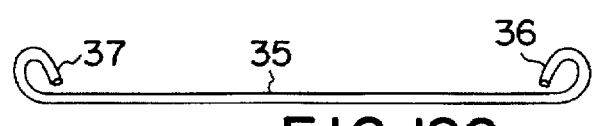
Figure 12D:
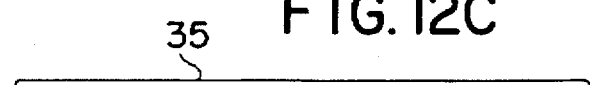

FIG. 11 shows a plan view of the preferred embodiment of the invention for tricuspid valve repair sutured in place in the typically enlarged tricuspid annulus (as described by Bex J P and Lecompte Y. "Tricuspid valve repair using a flexible linear reducer", J Cardiac Surg, 1:151, 1986). The tricuspid valve has an anterior leaflet 501, a posterior leaflet 502 and the septal leaflet 503. The junction of the septal and anterior leaflets is 504, the junction of the anterior and posterior leaflets is 505, and the junction of the posterior and septal leaflets is marked 506. The dotted line 507 shows the circumference of the annulus before pathologic dilatation.

The annuloplasty ring 200, is positioned such that colored marked 210 is approximately coincident with junction 504. Numerous interrupted sutures 508, are used to fix annuloplasty ring to the tricuspid valve annulus. The adjustable segment is delineated from drawstrings anchor points 208 to 209. Typically, this adjustable segment will approximately straddle a substantial portion of the posterior leaflet 502, as well as the junction of the posterior and anterior leaflets 505. It may also straddle an insubstantial portion of the anterior leaflet 501. The act of drawing in either or both drawstrings 204, 205 will cause the ring to contract between the drawstring anchor points 208 and 209. The amount of contraction will depend upon how much the drawstring is tightened, and whether only one or both drawstrings are tightened. By such means the enlarged circumference of the annulus may be reduced to that shown by dotted line 507. Following appropriate reduction the drawstring pairs are tied using a surgeon's knot which will lie between the ring and the annulus, out of the bloodstream.

Figure 16A:
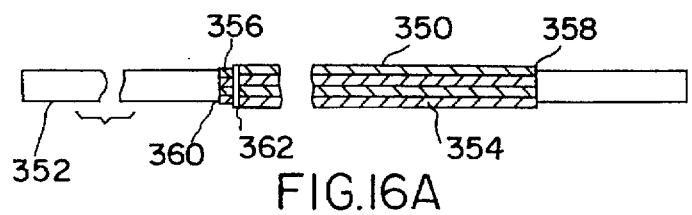
FIGS. 16A, 16B, 16C, 16D and 16E depict progressive steps in the formation of an invaginated braided tube used in forming the ring.

Referring now to FIGS. 16A–16E, the initial steps in manufacturing the braided ring is described. A pre-washed length of heat-setable, meltable braided fiber tubing 350, e.g. Atkins & Pearce braided polyester tape, is cut to the desired length, e.g. 250–290 mm, and the cut length is slid over a mandrel, rolled back onto a pusher rod 352 so as to form a double walled tube, having an inner wall 356 and an outer wall 354, approximately half the length of the original tubing. The tube has an inward fold 358 from outer wall 354 to inner wall 356 forming one end, the right end as depicted in FIG. 16A, the other ends of the tubing 360 and 362 lying generally adjacent each other.

Figure 16B:
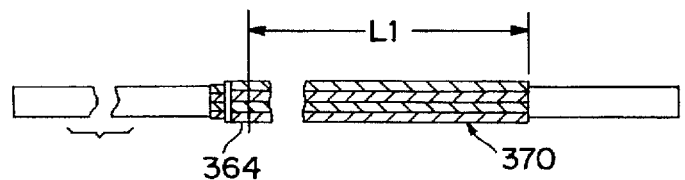

Referring to FIG. 16B, the double walled tube 370 is cut to a desired length, e.g. 112–133 mm, at 364 with a heated blade that cuts by melting the fibers and fusing the fibers together to form a fused end, the inner and outer walls being joined in an annular fused joint at 364.

Figure 16C:
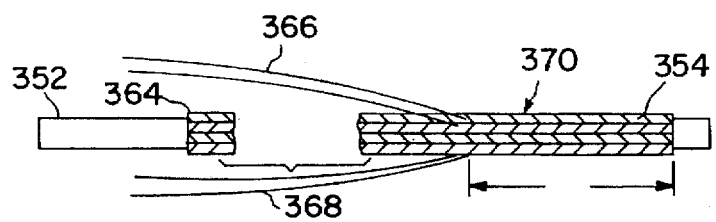

Referring to FIG. 16C, temporary sutures 366 and 368 are secured only through the outer layer 354 a desired distance, e.g. 56–66 mm from the end of the tube. The fused joint 364 is then rolled into the inside of the tube so as to turn a portion of the tube inside out, the temporary sutures being used to pull the layer through which they extend to roll the tube inside out to position the fused joint in the inside wall, preferably in the center of the inside wall of the tube 370. To clarify, the tube as shown in FIG. 16B, is rolled inside out so that the sealed-cut ends are on the right as shown in FIG.

Figure 16D:
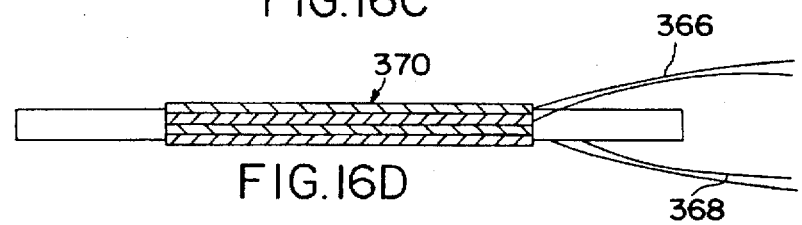
Figure 16E:

16C, the sutures are attached, and the tube is further rolled partially inside out until the sutures are at the right end as shown in FIG. 16D with the heat-sealed joint between the original ends of the tubing inside the final two-lay tube as shown in FIG. 16B.

The steps in forming the final tube are depicted in FIGS. 17A–17B and depict the steps of one facet of the invention, namely the method of manufacturing an annuloplasty or suture ring comprising the steps of invaginating tubing 350 braided of meltable, heat setable polymer fibers to form a tube 370 of an outer layer and an inner layer of tubing, a first end of the tube thus formed being defined by an annular, inward fold 358 of the tubing from the outer layer to the inner layer; forming a second end 364 of the tube by melting the inner and outer layers of tubing to fuse said layers together in an annular seal between said layers; and sliding said layers relative to each other defined new ends of annular, inward folds of tubing and to space the annular seal 364 distal from and between the newly formed ends inside the outer layer of the tube.

This double wall tube may be used in the devices of this invention, as a suture ring for heart valves and in any other device or method wherein a fabric suture strip, ribbon or ring is used to secure a prosthesis to tissue or to secure tissue to tissue.

Referring to FIGS. 18 and 19, the method, as used in making the aforementioned suture or annuloplasty rings, further comprises heat setting the thus formed tube 370 into a lateral V-shaped band 380 having a center heat set crease comprising four layers of tubing.

Reference is made specifically to FIG. 18 which depicts, in exploded view, the fixture for heat setting the tubing 370 into a V-shaped band 380. The double walled tube 370 is slipped over a V-shaped mandrel 372 which may be of metal or high temperature resistant polymer, e.g. polytetrafluoroethylene. The mandrel 370 carrying on it the tube 372 is clamped between forming tools 374 and 376 which define a V-shaped opening the size and shape of the desired V-shaped band. A pair of bolts, C-clamps, or any other clamping device may be used to secure the forming tools together. Bolt are preferred to maintain alignment of the tools. The clamped tools with the mandrel and tube are placed in an oven, or otherwise heated, to a temperature sufficient to heat set the polymer of which the tubing is formed without fusing it. In the case of polyester, temperatures in the range of 100°–110° C. are quite suitable in most instances. After a sufficient period, usually about ten minutes, to heat form the tubing, the clamped mandrel, with the tube in place, is first cooled to set the tube into a V-shaped band or tape 380 and then removed.

Figure 20:
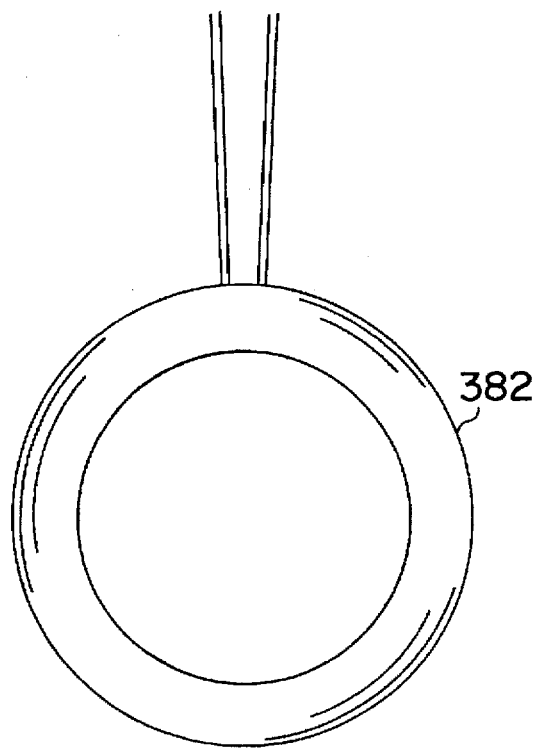
FIG. 20 depicts a suture ring suitable for use on prosthetic heart valves and other prosthetic devices. While a drawstring arrangement is not required for the suture ring, such an arrangement may be used, if desired, to secure the suture ring to the valve ring.
Figure 21:
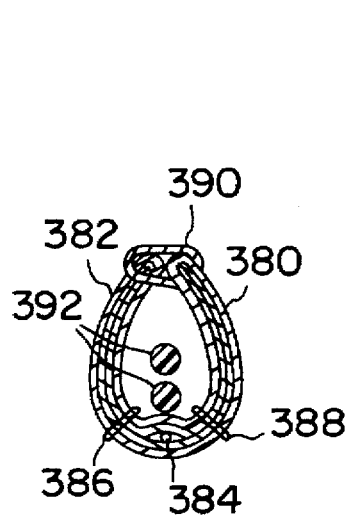
FIG. 21 depicts a cross-section of the suture ring of FIG. 20.
Figure 22:
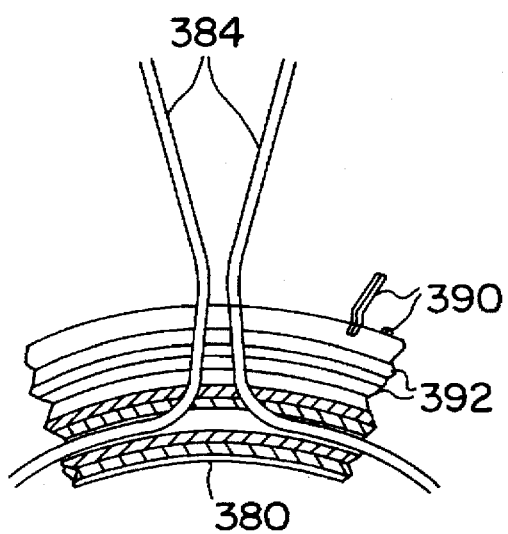
FIG. 22 depicts an enlarged view of the interior construction of a portion of the suture ring of FIG. 20 where the drawstrings exit, one-half of the ring fabric structure being cut away to expose the interior.

The V-shaped band may be secured end-to-end to define a suture ring, such as, for example, the suture ring 382 depicted in FIGS. 20–22. The suture ring 382 is formed of a length of V-shaped band or ribbon 380 secured end-to-end in any desired manner. Such a ring may be used for heart valve prostheses, for example. If desired, a drawstring 384 may extend through the tube, and through the tube walls, around the inner periphery of the suture ring. Pairs of demarcation seams 386 and 388 are sewn around the ring to maintain the drawstring in place and stabilize the ring. These demarcation seams may be of different colors thereby identifying the respective sides of the ring. The ring is closed at a first outer periphery by closure suture 390. In use, the drawstring may be a heat-shrink type monofilament or polyfilament string. The ring is placed on the prosthesis, the drawstring 384 tightened and tied. The prosthesis may then be heated causing the drawstring to form an extraordinarily tight and strong securement of the ring to the prosthesis. The use of a heatshrink drawstring is not necessary, of course. In some applications, where x-ray identification or location of the suture ring is desirable, a radiopaque fiber is wrapped two or more times around the ring or placed such that the two or more fibers lie adjacent each other.

The invention, as described, may be in the form of a suture ring for use in surgery for securing a prosthesis in or adjacent to an annular organ structure or stabilizing or shaping a generally annular organ portion. The suture ring comprises an elongate braided biocompatible ribbon 380 having ends, elongate edges and a central portion, the lateral cross-section of the ribbon generally defining a V-shape, the edges extending outwardly from the center, means securing the respective ends of the ribbon together thereby configuring the ribbon generally into an annulus, the central portion defining the internal periphery of the annulus, the edges extending outwardly from said internal periphery. The ring may be provided with at least one drawstring 384 extending around at least a portion of the annulus and through the ribbon selectively to decrease the diameter of the internal periphery of the annulus, the drawstring being disposed adjacent said center, the edges extending outwardly from the drawstring. The drawstring may be omitted and the ring secured to a valve using one or more wraps of heat-shrinkable material, e.g. polyester, to tye the ring to the valve. Means are provided for securing the edges of the ribbon together, the edges of the ribbon defining the external annulus periphery. The drawstring and ribbon-like member are so constructed and configured that when the draw-string is drawn the internal diameter of the annulus contracts and the width of the annulus increases thereby substantially preventing the ribbon-like member from gathering into irregular clumps as the internal diameter of the annulus contracts.

The ability of the ring to contract in its interior annulus without bunching, gathering or folding is a great advantage. The construction described permits the excess material to expand laterally outwardly as necessary without bunching.

The method of use of is as follows. The left atrium is exposed following a mid-line sternotomy, and cardiopulmonary bypass established using conventional techniques. A left ventricular drain may be inserted into the apex of the left ventricle. The aorta is cross-clamped and a cold cardioplegia solution is pumped into the aortic root causing the heart to be cooled and inducing cardiac arrest. Alternatively, retrograde cardioplegia may be given via the coronary sinus. An incision is made into the left atrium, exposing the damaged mitral valve. The technique so far described is a general description of mitral valve exposure, and is not specific to the particular device.

Surgical techniques of implantation vary between centers. The surgeon will then carefully examine the mitral valve mechanism to ascertain if the valve is amenable to repair, and if so, what the mechanism of repair will be. For example, the lesion may be at the level of the annulus, leaflets, chordae, or papillary muscles. The appropriate surgical repair procedure will depend upon the pathology found. In cases where the annulus is enlarged, or where a segment has been removed from the mitral valve leaflets, the mitral valve annuloplasty ring will be implanted as part of the repair procedure. First the appropriate size ring is chosen using the sizer set supplied for this purpose. Interrupted sutures are placed at the fibrous trigones, between the trigones, and around the remaining circumference of the annulus. The sutures are passed through corresponding portions of the annuloplasty ring, outside the line of demarcation, marked by the colored suture line on the atrial side of the annuloplasty ring. The ring is then pushed down the sutures until it lies on the annulus. Each interrupted suture is tied and cut. Mitral valve competency is then assessed by suitable means (e.g. by the injection of a saline solution through the left ventricular drain, or by removing the aortic cross-clamp and temporarily rendering the aortic valve incompetent). If the mitral valve is regurgitant the areas of reflux are noted. If leakage occurs in the right posterior leaflet, this area of the ring is contracted by gently pulling on one or both of the drawstrings in this region of the ring. It may be necessary to tighten one or both drawstrings pairs depending upon the individual valve pathology. Mitral valve competence is again assessed, and if necessary further adjustments made.

When the surgeon is satisfied that an optimum mitral valve competence has been achieved without compromising mitral valve opening area the drawstrings are tied as pairs. The surplus portions of the drawstrings are cut close to the knots. Mitral valve competence is then confirmed. At this stage, should any slight reflux be present, it can be eliminated or minimized by placing one or more plicating sutures at the appropriate portion of the annuloplasty ring. However, should a drawstring have been inadvertently over-tightened, it may be cut below the knot to release the constricting segment. That portion of the ring might then need to be shortened by the placement of sufficient plicating sutures. The left atrium is then closed, air removed from the heart, warm blood allowed to reperfuse the coronary tree, the heart defibrillated if necessary, and the patient slowly weaned from cardiopulmonary bypass. Implantation of the tricuspid ring follows a similar course with variations appropriate to the different anatomy and the corresponding differences in the tricuspid and mitral annuloplasty rings.

References Cited
UNITED STATES PATENTS

| | | |
|---|---|---|
| 3,491,376 | 01/1970 | Shiley |
| 3,534,411 | 10/1970 | Shiley |
| 3,656,185 | 4/1972 | Carpentier |
| 4,042,979 | 8/1977 | Angell |
| 4,055,861 | 11/1977 | Carpentier et al. |
| 4,164,046 | 8/1979 | Cooley |
| 4,217,665 | 8/1980 | Bex et al. |
| 4,263,680 | 04/1981 | Muller, et al. |
| 4,290,151 | 9/1981 | Massana |
| 4,339,831 | 7/1982 | Johnson |
| 4,451,936 | 06/1984 | Carpentier, et al. |
| 4,606,911 | 7/1986 | Ahmadi et al. |
| 4,702,250 | 10,1987 | Levy, et al. |
| 4,477,930 | 10/1984 | Totten, et al. |
| 4,865,600 | 09/1989 | Carpentier, et al. |
| 4,888,009 | 12/1989 | Lederman, et al. |
| 4,917,698 | 4/1990 | Carpentier et al. |
| 5,104,406 | 04/1992 | Curcio, et al. |
| 5,104,407 | 04/1992 | Lam et al |

PUBLICATIONS

Tsakiris A G. "The physiology of the mitral valve annulus". in The mitral valve—a pluridisciplinary approach. ed Kalmanson D. Publishing Sciences Group, Acton, Mass., pg 21, 1976.

Geller M, Kronzon I, Slater J et al. "Long-term follow-up after mitral valve reconstruction: incidence of postoperative left ventricular outflow obstruction". Circulation, 74:I-99, 1986.

Carpentier A, Deloche A, Hanania G, et al. Surgical management of acquired tricuspid valve disease. J Thorac Cardiovasc Surg, 67:53, 1974.

Duran C D, and Ubago J L M. "Clinical and Hemodynamic Performance of a Totally Flexible Prosthetic Ring for Atrioventricular Valve Reconstruction" Annals of Thoracic Surgery, 22:458, 1976.

Levine, R. A., Triulzi, M. O., Harrigan P., and Weyman, A. E. "The relationship of mitral annular shape to the diagnosis of mitral valve prolapse". Circulation, 75:756, 1987.

Bex J P and Lecompte Y. "Tricuspid valve repair using a flexible linear reducer", J Cardiac Surg, 1:151, 1986.

What is claimed is:

1. A suture ring for use in surgery for securing a prosthesis in or adjacent to an annular organ structure or stabilizing or shaping a generally annular organ portion comprising, in combination:

an elongate braided biocompatible ribbon having ends, elongate edges and a central portion the lateral cross-section of the ribbon generally defining a V-shape the edges extending outwardly from the central portion, means securing the respective ends of the ribbon together thereby configuring the ribbon generally into an annulus, the central portion defining the internal periphery of the annulus, the edges extending outwardly from said internal periphery;

at least one drawstring extending around at least a portion of the annulus and through the ribbon selectively to decrease the diameter of the internal periphery of the annulus, the drawstring being disposed adjacent the central portion, the edges extending outwardly from the drawstring; and means securing the edges of the ribbon together, the edges of the ribbon defining the external annulus periphery;

the drawstring and ribbon being so constructed and configured that when the draw-string is drawn the internal diameter of the annulus contracts and the width of the annulus increases thereby substantially preventing the ribbon from gathering into irregular clumps as the internal diameter of the annulus contracts.

* * * * *